(12) United States Patent
Kaufmann et al.

(10) Patent No.: US 9,964,506 B2
(45) Date of Patent: May 8, 2018

(54) SENSOR SYSTEM FOR DETERMINING THE MOISTURE CONTENT OF A FLUID MEDIUM FLOWING IN A MAIN FLOW DIRECTION

(71) Applicant: Robert Bosch GmbH, Stuttgart (DE)

(72) Inventors: Andreas Kaufmann, Sontheim An der Brenz (DE); Ulrich Wagner, Munich (DE); Lukas Hagmanns, Mutlangen (DE); Achim Briese, Rutesheim (DE)

(73) Assignee: ROBERT BOSCH GMBH, Stuttgart (DE)

( * ) Notice: Subject to any disclaimer, the term of this patent is extended or adjusted under 35 U.S.C. 154(b) by 16 days.

(21) Appl. No.: 14/434,642

(22) PCT Filed: Sep. 16, 2013

(86) PCT No.: PCT/EP2013/069132
§ 371 (c)(1),
(2) Date: Apr. 9, 2015

(87) PCT Pub. No.: WO2014/060161
PCT Pub. Date: Apr. 24, 2014

(65) Prior Publication Data
US 2015/0260672 A1    Sep. 17, 2015

(30) Foreign Application Priority Data

Oct. 15, 2012  (DE) .................... 10 2012 218 758

(51) Int. Cl.
*G01N 27/12*  (2006.01)
*F02D 41/18*  (2006.01)
(Continued)

(52) U.S. Cl.
CPC .......... *G01N 27/121* (2013.01); *F02D 41/18* (2013.01); *F02M 35/10393* (2013.01);
(Continued)

(58) Field of Classification Search
CPC .............. G01N 27/121; G01N 27/223; G01N 33/0004; F02D 41/18; F02D 2041/1472; F02M 35/10393
(Continued)

(56) References Cited

U.S. PATENT DOCUMENTS 1,810,693 A * 6/1931 Alfaro ..................... B64C 21/02
                                                    244/204
6,581,447 B1 * 6/2003 Strohrmann ............ F02D 41/18
                                                    73/114.31
(Continued)

FOREIGN PATENT DOCUMENTS

DE    10 2008 02973    10/1999
DE    10 2010 043 062   5/2012
(Continued)

OTHER PUBLICATIONS

International Search Report for PCT/EP2013/069132, dated Nov. 18, 2013.
(Continued)

*Primary Examiner* — Peter Macchiarolo
*Assistant Examiner* — Irving A Campbell
(74) *Attorney, Agent, or Firm* — Norton Rose Fulbright US LLP; Gerard Messina

(57) ABSTRACT

A sensor system for determining a moisture content of a fluid medium flowing in a main flow direction, e.g., an intake air of an internal combustion engine, includes: a sensor housing; at least one moisture sensor situated in the sensor housing for determining the moisture content of the fluid medium; at least one retaining element at least partially permeable to moisture; an inlet opening for channeling moisture into the sensor housing and to the moisture sensor; and at least one outlet opening situated separately from the inlet opening and channeling moisture from the sensor
(Continued)

housing into the flowing fluid medium. The retaining element is situated in the sensor housing in such a way that the moisture sensor is acted upon by the moisture via the inlet opening and the retaining element.

14 Claims, 6 Drawing Sheets

(51) Int. Cl.
*F02M 35/10* (2006.01)
*G01F 5/00* (2006.01)
*G01N 27/22* (2006.01)
*G01N 33/00* (2006.01)
*F02D 41/14* (2006.01)

(52) U.S. Cl.
CPC .............. *G01F 5/00* (2013.01); *G01N 27/223* (2013.01); *G01N 33/0004* (2013.01); *F02D 2041/1472* (2013.01)

(58) Field of Classification Search
USPC .......................................... 73/29.05, 335.04
See application file for complete search history.

(56) References Cited

U.S. PATENT DOCUMENTS

| | | | |
|---|---|---|---|
| 7,946,151 B2* | 5/2011 | Butt | H01M 8/04007 73/29.02 |
| 7,980,126 B2* | 7/2011 | Opitz | G01F 1/6986 73/204.26 |
| 2014/0076026 A1* | 3/2014 | Starling | G01N 27/00 73/29.02 |

FOREIGN PATENT DOCUMENTS

| | | |
|---|---|---|
| EP | 2 154 494 | 2/2010 |
| EP | 2 439 499 | 4/2012 |
| EP | 2 487 355 | 8/2012 |
| WO | WO 2011/070535 | 6/2011 |

OTHER PUBLICATIONS

Konrad Reif (Edtr.): Sensors in the Motor Vehicle, 1$^{st}$ edition 2010, pp. 98-101.

* cited by examiner

SENSOR SYSTEM FOR DETERMINING THE MOISTURE CONTENT OF A FLUID MEDIUM FLOWING IN A MAIN FLOW DIRECTION

BACKGROUND OF THE INVENTION

1. Field of the Invention

The present invention relates to a sensor system for determining the moisture content of a fluid medium flowing in a main flow direction.

2. Description of the Related Art

Numerous methods and devices for determining at least one property of a flowing fluid medium, that is, liquids and/or gases, are known from the related art. The properties, as possible parameters, may basically be any physically and/or chemically measurable properties which qualify or quantify a flow of the fluid medium, in this context. In particular, this may be about a flow speed and/or a mass flow and/or a volume flow. One further property of the flowing fluid medium is the moisture content.

The field of the present invention will be described below, particularly with reference to so-called moisture sensors, as described, for example, in Konrad Reif (Edtr.): Sensors in the Motor Vehicle, $1^{st}$ edition 2010, pages 98-101.

Such a moisture sensor may be situated in a housing of its own sensor system or in a housing of a so-called hot-film air-mass sensor. Such a setup is described, for example, in German patent application document DE 10 2010 043 062 A1. In this case, the moisture sensor is accommodated in the sensor housing of the hot-film air mass sensor. The sensor housing has an inlet opening for the moisture which is closed by a semipermeable membrane. The moisture penetrates the membrane and thereby reaches the moisture sensor on the inside of the sensor housing. The membrane is provided to retain dirt particles, in this context.

Despite the numerous advantages of the methods and devices, known from the related art for detecting the moisture content, they still include room for improvement. The danger in the above systems is that the membrane of the moisture sensor may be contaminated during operation by water, dust or oil mist, for example. This causes less moisture to reach the moisture sensor than in the case of an uncontaminated membrane. This is able to lead to errors in the determination of the moisture content.

BRIEF SUMMARY OF THE INVENTION

A sensor system is therefore provided for determining the moisture content in a fluid medium flowing in the main flow direction, which is able to avoid, at least to a great extent, the disadvantages of known methods and strategies, and in which the danger of contamination of a membrane is able to be avoided, whereby the accuracy of the determination of the moisture content is improved.

The sensor system for determining a moisture content of a fluid medium flowing in the main flow direction, particularly of the intake of an internal combustion engine, includes a sensor housing, particularly a plug sensor introduced, or able to be introduced into a flow tube, at least one moisture sensor situated in the sensor housing for determining the moisture content of the fluid medium and at least one retaining element, the retaining element being at least partially permeable to moisture; the sensor system having an inlet opening for moisture into the sensor housing, and the moisture sensor and the retaining element being situated in the sensor housing in such a way that the moisture sensor is able to have moisture applied to it via the inlet opening and the retaining element; the sensor system having at least one outlet opening situated separately from the inlet opening, for moisture from the sensor housing into the flowing fluid medium.

The inlet opening may be located downstream from the outlet opening, as seen in the main flow direction. The retaining element may at least partially span the moisture sensor. Between the inlet opening and the outlet opening, the retaining element may be able to be flowed over by the fluid medium counter to the main flow direction (e.g., in a direction anti-parallel to the main flow). The moisture sensor may have a measuring surface, the sensor housing being developed in such a way that inside the sensor housing, between the inlet opening and the outlet opening, the measuring surface of the moisture sensor is able to be flowed over in parallel by the fluid medium. The sensor housing is able to have a channel, the channel being situated between the inlet opening and the outlet opening, the moisture sensor being situated in the channel. The sensor housing may have a leading edge that points towards the fluid medium. The sensor housing may be developed so that the fluid medium flows faster in the vicinity of the outlet opening than in the vicinity of the inlet opening. The sensor housing may be developed so that the fluid medium flows faster in the vicinity of the outlet opening than in the vicinity of the inlet opening. At least between the inlet and the outlet, the sensor housing may essentially have the form of an airfoil profile, the inlet opening and the outlet opening being situated downstream or upstream, for example, of the airfoil profile. The flow contour between the inlet opening and the outlet opening, that is, for example, airfoil-shaped, has mainly the tasks of generating as large as possible a pressure difference for flowing through the channel between the inlet opening and the outlet opening as well as implementing a centrifugal separation for particles and droplets. In this context, the conditions of the entire sensor system, particularly the dimensions of the sensor housing should be taken into account. One-deviation from airfoil profiles, which are customary in the airplane field, is that in the area of the inlet opening, a zone of high static pressure is deliberately generated, and in this area, in a targeted manner, no flow is developed lying against the contour. In the area of the outlet opening, on the other hand, as low as possible a static pressure is supposed to be developed at correspondingly high flow speeds. Therefore, the statement of the airfoil shape for the area between the inlet opening and the outlet opening relates to the description of the bodily form or the outer looks, but not to the method of functioning, as it is known from aerodynamics. The inlet opening and the outlet opening may essentially be developed to be slot-shaped. In the sensor housing, a bypass channel may be developed, the sensor housing having an inlet into the bypass channel, which points counter to the main flow direction (e.g., in a direction anti-parallel to the main flow) and at least one outlet from the bypass channel of the sensor housing, the sensor system further being able to have an additional sensor for determining at least one additional parameter of a fluid medium flowing through the bypass channel, particularly of an intake air mass of an internal combustion engine, the sensor having at least one sensor chip, situated in the bypass channel, for determining the additional parameter of the fluid medium.

Within the scope of the present invention, one should understand by main flow direction the local flow direction of the fluid medium at the location of the sensor, or the sensor system, whereby local irregularities, for example, such as turbulences, are able to remain disregarded. Consequently, by main flow direction one may, in particular, understand the local averaged transport direction of the flowing fluid medium, at the location of the sensor system. In this context, the average transport direction relates to a transport direction in which the fluid medium flows predominantly in the average time.

Within the scope of the present invention, by a moisture sensor one should understand any sensor element which is designed to detect a moisture of the fluid medium. In this instance, for example, resistive or capacitive sensor elements known from the related art come into consideration. Examples of such sensors are known from Konrad Reif (publisher): Sensors in the Motor Vehicle, 1st edition 2010, pages 98-101. Other types of moisture sensors may, however, basically come into consideration alternatively or additionally for use within the scope of the present invention. The moisture content may, in this context, be expressed as an absolute value, in grams of water per kilogram or cubic meter of air, for example. Alternatively or in addition, the moisture content may be expressed as relative air moisture in percent. Within the scope of the present invention, by relative air moisture one should understand the percentage ratio of the instantaneous vapor pressure of the water and the saturation vapor pressure of same at the air temperature. The relative humidity tells directly to what degree the air is saturated with water vapor.

Within the scope of the present invention, by a retaining element one should understand any element that is designed to hold back at least larger contamination such as dust particles, dirt, liquid drops or similar larger contamination, having a size, for instance, of more than 0.2 mm, preferably more than 0.5 mm, whereas moisture of the fluid medium, such as the air humidity, is able to penetrate the retaining element. The retaining element may particularly include at least one moisture-permeable membrane, for instance, a plastic membrane and/or at least one web, for instance, at least one net, for example.

By the statement "in the vicinity of" for a position, within the scope of the present invention, one should understand a position which extends within a plane perpendicular to the main flow direction, and includes the referenced component mentioned. For instance, the statement that the fluid medium has a certain pressure in the vicinity of the inlet opening, means a position, at which the pressure is determined, which is within the plane which runs perpendicular to the main flow direction, and includes an effective area of the inlet opening. By an effective area of the inlet opening one should understand the area of the inlet opening itself and its immediate environment. That is why, in the vicinity of the inlet opening, an effective, relatively high averaged static pressure, in connection with an effective, relatively low averaged static pressure in the vicinity of the outlet opening, drives the flowing through the channel.

Within the scope of the present invention, by the term "downstream" one should understand a system in which the component named in connection with this term is reached, by the fluid medium flowing in the main flow direction, at a later time than a reference component. For example, the statement, that the inlet opening is located downstream from the outlet opening, means that the fluid medium flowing in the main flow direction, from a point of view of time, first reaches the outlet opening and then the inlet opening.

Within the scope of the present invention, by the term "upstream" one should understand a system in which the component named in connection with this term is reached, by the fluid medium flowing in the main flow direction, at an earlier time than a reference component. For example, the statement, that the outlet opening is located upstream of the inlet opening, means that the fluid medium flowing in the main flow direction, from a point of view of time, first reaches the outlet opening and then the inlet opening.

Within the scope of the present invention, by the shape of an airfoil profile, one should understand a shape which, in a side view approximately has the form of an airfoil, i.e. having opposite arched side areas in the main flow direction. In this context, the side areas may have different curvatures or arching. Transversely to the main flow direction, changeable or unchangeable contours are conceivable. The contour of the side area lying downstream, which is also located directly upstream of the inlet opening, may be designed so that the flow separates there, which is achieved by a contour which is sloped back clearly but steadily, that is, free of jumps with respect to the curvature. A contour designated in the mechanics of flow literature as a rebounding step, that is, a contour changing abruptly, at which the flow cross section abruptly increases at the abrupt location, is also conceivable. However, there is created at such a rebounding step a geometrically induced flow separation, having downstream a rather thin flow shearing cut and a rather stable recirculation zone, into which only relatively little fluid of the outer flow is mixed in. That is, the moisture content of the outer flow to be measured is not present directly in the area of the inlet opening. In this regard, a stronger mixing through should be more favorable, without, however, conveying fluid particles or solid particles into the inlet.

Within the scope of the present invention, by the pressure one should understand the amount of a force perpendicular to an area per area content of the area. The pressure in flowing media is composed of a static and a dynamic proportion. While both parts are a function of the density, they differ in that the static pressure, for fluids having a constant density, increase linearly with the height of the fluid column above the area. In addition, it is a function of the Earth's gravitational acceleration. By contrast, the dynamic portion increases quadratically with the flow speed of the fluid. In a friction-free flow, a constancy of the sum is made up of a dynamic and a static proportion. This is the consequence of the conservation of energy in the flow, and is known for this special case as Bernoulli's Law.

Within the scope of the present invention, by static pressure one should understand the condition of a force, exerted on each area which is in connection with the fluid, which acts in proportion to the size of the area. The static pressure may be ascertained, for instance, with the aid of the equation Pstat.=$\rho*g*h$, where $\rho$ is the density of the fluid, g is the Earth's gravitational acceleration and h is the height of the fluid column over the area.

Within the scope of the present invention, by the dynamic pressure one should understand the value resulting from the kinetic energy of a flowing fluid at the surface of a body in this flow. The dynamic pressure may be ascertained with the aid of the equation Pdyn.=$0.5*\rho*v^2$, where $\rho$ is the density of the fluid and v is the speed of the fluid. Thus, the dynamic pressure increases and decreases with the speed of the fluid. However, going from larger to smaller cross sectional areas, the speed is only able to increase if the static pressure in the smaller cross sectional areas is lower, and vice versa. That is, during the transition from a larger to a smaller cross sectional area, a dynamic decrease in the static pressure is created at a simultaneous increase in the dynamic pressure. In reverse to this, the static pressure increases at a transition from a smaller to a larger cross sectional area, while the dynamic pressure drops. To be sure, as a rule, the dynamic pressure cannot be measured directly, but it is used for the speed measurement of the fluid.

Within the scope of the present invention, the sensor system may include one sole moisture sensor. It is also possible, however, that additional sensors are included by the sensor device, such as a hot film air mass sensor and/or a temperature sensor and/or a pressure sensor.

Within the scope of the present invention, the moisture sensor may be integrated into a housing of a hot film air mass sensor, as is described, for example, in Konrad Reif (Edtr.): Sensors in the Motor Vehicle, $1^{st}$ edition 2010, pages 146-148. Such hot film air mass sensors are based, as a rule, on a sensor chip, especially a silicon sensor chip, having a sensor membrane as measuring surface or sensor area over which the flowing fluid medium flows, for example. As a rule, the sensor chip includes at least one heating element as well as at least two temperature sensors which, for instance, are situated on the measuring surface of the sensor chip, one temperature sensor being supported upstream of the heating element and the other temperature sensor being supported downstream from the heating element. From an asymmetry of the temperature profile recorded by the temperature sensors, which is influenced by the flow of the fluid medium, one may draw a conclusion on a mass flow and/or a volume flow of the fluid medium.

Hot film air mass sensors are usually designed as plug-gable sensors which are able to be applied in a fixed manner or exchangeably in a flow tube. This flow tube may, for instance, be an intake tract of an internal combustion engine.

Because of the present invention, the retaining element, which may be developed in the form of a protective membrane, is protected from direct contact with particles and droplets, at the same time, a sufficient flowing over by air being assured.

Thus the moisture is able to be measured correctly, and the functioning of the moisture sensor is ensured even in an environment which is greatly contaminated, for example, by particles, water drops or oil vapor. This may be achieved by the special flow technological positioning of inlet and outlet slots on the cover of the sensor housing that is otherwise closed, in combination with a special profile, which generates overpressure at the inlet and underpressure at the outlet. In a corresponding manner, the functionally determined elements of the sensor housing, such as the leading edge of the plug sensor, as well as the outlet slot and the flow contour of the cover are designed in such a way that the protective membrane is no longer exposed directly to the fluid medium. At a correct execution of the flow contour of the cover, flow relationships and pressure relationships come about at the protective membrane of the moisture sensor, which are such that the inlet slot is located in a zone in which the flow is slowed down, or rather, a slight flow speed prevails and/or the boundary layer has separated, and thus there is present a relatively high static pressure, and the outlet opening is located in a zone in which the flow is accelerated, and a high flow speed is present. Because of the flow field-defining action of the sensor housing and of the cover having the special profile, there comes about a favorable system having the inlet slot in the downstream and the outlet slot in the upstream part of the cover. With that, the protective membrane is flowed through counter (e.g., in a direction anti-parallel to the main flow) to the main flow direction.

Thus, the zone into which the air is taken in, is largely free of particles or droplets, since these, based on their inertia, cross the zone at lower air speed, or do not reach it at all, and continue to fly in the main flow direction. Consequently, the air which is conveyed past the protective membrane of the sensor element is largely freed of particles and droplets, and this avoids contamination. One essential element for generating the flowing through is the contour of the cover in connection with the leading edge of the plug sensor. One suitable design is characterized in that the flow at the inlet slot is slowed down and speeded up at the outlet slot. This may be achieved by an airfoil-like profile. For example, the flow contour may be shaped solely by the cover. Alternatively, the leading edge, that is, the upstream end face of the sensor housing may be included in the design. It is also conceivable that a shape is derived from the wing profile. This may be further improved by chimneys on the outlet. However, a more edgy execution is also conceivable, which may be constructively easier to implement. The contour in the inner region, i.e. on the inside of the sensor housing, particularly in the immediate proximity of the measuring element, is a further aspect to be taken into consideration. Because of the advantageous embodiment of the inner contour, there comes about as high as possible a mass flow in the direct proximity, that is, the flow layer of the measuring element that is close to the wall. This air mass flow, that is as great as possible, is striven for in order to be able to determine the actually present air moisture at as small as possible a delay, that is, as small as possible a time duration up to the required magnitude of the signal step response.

In order to achieve this, the air should be guided as parallel as possible to the surface of the measuring element. Separations at the front edge of the measuring element with reference to the flowing through in the inner region as well as the flow-back regions or dead water zones above the measuring element should be avoided. Such flow-back regions or dead water zones may include a circulating air mass, whose moisture does not correspond to the currently present moisture that is to be measured. Because of such areas, there come about unnecessary idle times with respect to the signal values. Corresponding variants of the inner contour of the cover do not run parallel to the outer contour, but are rather parallel to the measuring element. The channel coming about between the measuring element and the cover may, in turn, not be too small, because otherwise a high flow-through resistance would come about.

Furthermore, it may be advantageous to shape the front edge on the measuring element in a manner favorable to flow, that is, rounded off, for instance, or by an extruded-on chamfer, so as to avoid a backflow region described. In this context, the front edge is the edge which faces the partial flow of the fluid medium through the inlet opening into the inside of the sensor housing.

DETAILED DESCRIPTION OF THE INVENTION

Figure 1:
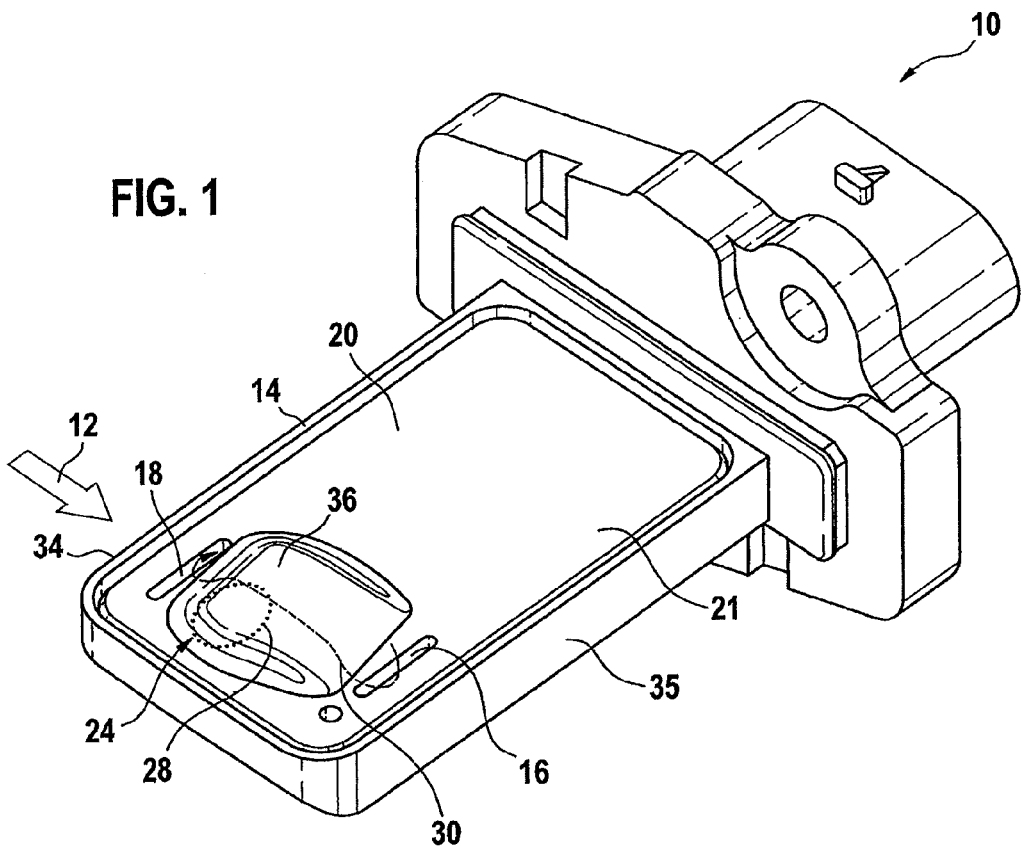
FIG. 1 shows a perspective illustration of a sensor device according to the present invention.

FIG. 1 shows a first specific embodiment of a sensor system 10 for determining a moisture content of a fluid medium flowing in a main flow direction 12, especially of intake air of an internal combustion engine. In this exemplary embodiment, sensor system 10 includes a sensor housing 14 which may be developed as a plug sensor, for example, which is able to be plugged or integrated into a flow tube, particularly an intake tract of the internal combustion engine. Sensor system 10 includes an inlet opening 16 and an outlet opening 18 into, and out of sensor housing 14. Inlet opening 16 and outlet opening 18 are developed in a cover 20 of sensor housing 14. In the exemplary embodiment shown, inlet opening 16 and outlet opening 18 are located in the cover 20 on a side which extends in parallel to main flow direction 12 and a longitudinal extension direction of sensor housing 14 which, with reference to the representation in FIG. 1, is an upper side 21, for instance. Upper side 21, for example, is a side which extends perpendicular to a side facing in the main flow direction 12. Thus, cover 20 is situated on upper side 21 of sensor housing 14, or rather, defines it. In a state in which cover 20 is set into sensor housing 14, inlet opening 16 is located downstream from outlet opening 18, as seen in main flow direction 12. For instance, inlet opening 16 and outlet opening 18 are developed to be slot-shaped, the dimensions of the slot-shaped opening cross section, as seen in main flow direction 12, in each case being able to amount to 1.5 mm, for example. The slots may have rounded or sharp edges on the inner side and/or the outer side.

Figure 2:
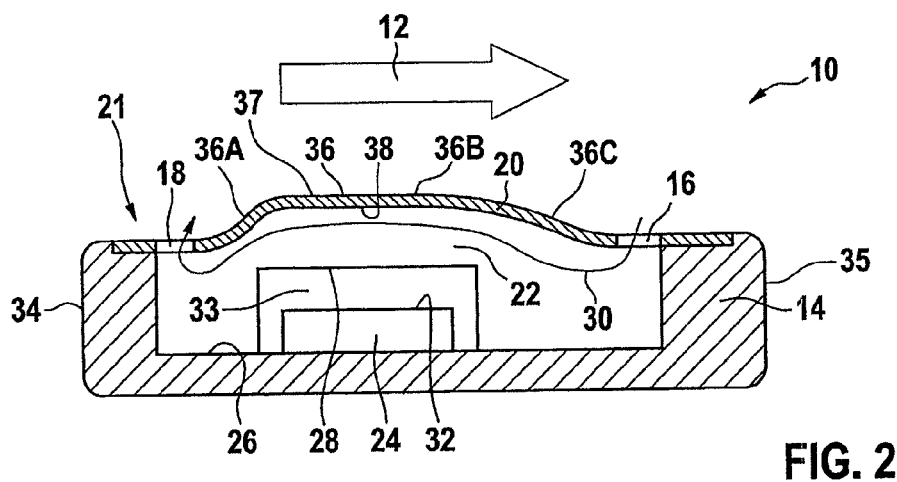
FIG. 2 shows a cross sectional view of the sensor device.
Figure 3:
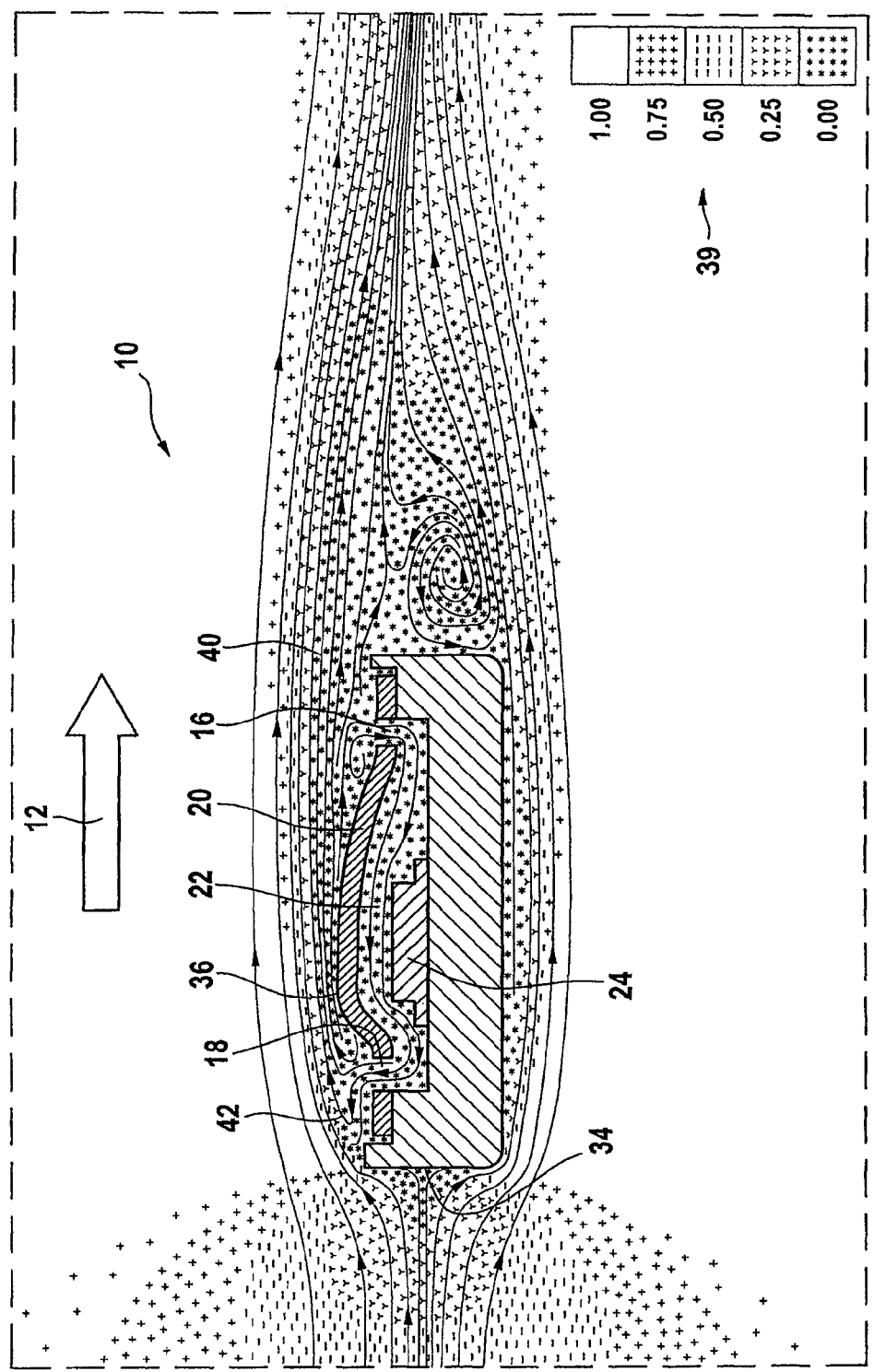
FIG. 3 shows a schematic representation of the distribution of the flow speeds during flowing around the sensor system.

As one may see in FIG. 2 or FIG. 3, a channel 22 is formed on the inside of sensor housing 14, between inlet opening 16 and outlet opening 18. A moisture sensor 24 is situated on the inside of sensor housing 12. Moisture sensor 24 is situated in channel 22. Moisture sensor 24 is at a distance from cover 20. For example, moisture sensor 24 is situated on a wall 26, of channel 22, that is opposite cover 20. Moisture sensor 24 is spanned by a retaining element 28, such as a membrane. FIG. 2 shows, for example, that within sensor housing 14, moisture sensor 24 is flowed over in a flow direction 30 that is opposite to the main flow direction 12. In particular, moisture sensor 24 has a measuring surface 32 which faces channel 22. Moisture sensor 24 is situated in such a way that the fluid medium is able to flow over it in as parallel a manner as possible. A small gap is provided between moisture sensor 24 and retaining element 28. Gap 33 is formed particularly between measuring surface 32 and retaining element 28. However, gap 33 may also be provided at the side surfaces of moisture sensor 24, i.e., with reference to the illustration in FIG. 2, to the left and the right of moisture sensor 24.

Sensor housing 14 has a leading edge 34, which faces counter to the fluid medium flowing in main flow direction 12, and forms an end face of sensor housing 14. Leading edge 34 extends perpendicular to main flow direction 12, for example. Furthermore, at its downstream end, as seen in main flow direction 12, sensor housing 14 has a rear edge 35, which extends perpendicular to main flow direction 12. Cover 20 includes at least one region 36 between inlet opening 16 and outlet opening 18, for instance, which is developed approximately in the form of an airfoil profile. Consequently, region 36, as seen in main flow direction 12, is formed by a leading edge 36A, which rises, and thus moves away from sensor housing 14 with increasing motion in the main flow direction 12, by a flow-over region 36B which extends essentially in parallel to main flow direction 12 and by a flow-away region 36B, which drops off as seen in main flow direction 12, and thus approaches sensor housing 14 with increasing motion in main flow direction 12. With respect to main flow direction 12, cover 20 may be developed upstream of outlet opening 18 and downstream from inlet opening 16 in parallel to main flow direction 12. In this context, inlet opening 16 and outlet opening 18 are situated downstream and upstream, respectively, of the special profile of region 36. Thus, region 36 has an upper side 36 that projects in an arched manner from sensor housing 14, which is exposed to the fluid medium that flows in the main flow direction 12, and a lower side 38, lower side 38 of region 36 facing toward channel 22 and thus being exposed to the fluid medium flowing in the direction of arrow 30. The special profile of region 36 is distinguished by the fact that, upstream at outlet opening 18 it generates a lower static pressure than downstream at inlet opening 16, and thereby drives the flow in channel 22 in a causative manner.

Because of the development or the shape described of sensor system 10, there comes about the distribution of the flow speed shown in FIG. 3. In FIG. 3, in this context, flow lines and flow regions are drawn in to which certain flow speeds are assigned. The respective flow speeds are shown on scale 39 of FIG. 3, in which the flow speed is entered in meters per second (m/s). From this it becomes clear that inlet opening 16 is located in a flow range 40 in which the flow is slowed down and/or a flow boundary layer is separated, and thus high static pressures are present. Outlet opening 18 is located in a flow region 42, in which high flow speeds and therefore low static pressures are present. And thus, a deceleration takes place from flow region 42 near leading edge 34 on outlet opening 18 of ca. 0.75 m/s to ca. 0.25 m/s in flow region 40 of inlet opening 16.

Figure 4:
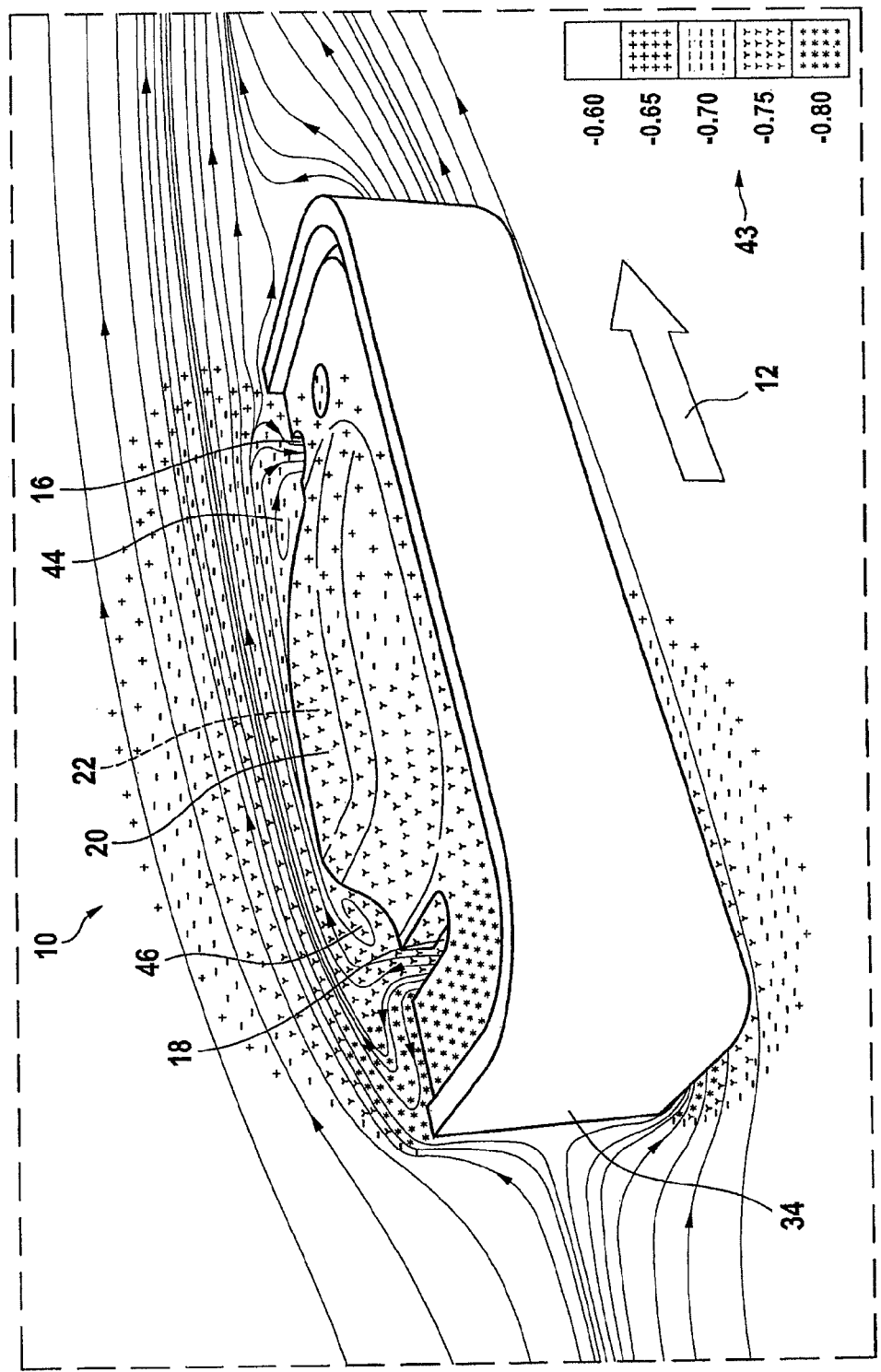
FIG. 4 shows a schematic representation of the pressure distribution during flowing around the sensor system.

FIG. 4 further shows the distribution of the static pressure in a cross section in the case of a development of sensor system 10 according to the present invention. In FIG. 4, the flow lines have been drawn in, in addition. The development of the flow lines corresponds to the planar distribution of the pressure. The respective pressures are shown on scale 43 of FIG. 4, in which the flow speed is entered in Pascals (Pa). This is about a relative pressure to the absolute environmental pressure of 1 bar. For reasons of numerical accuracy, in flow simulations people frequently deal with relative pressures, which may subsequently be determined again to form an absolute pressure, based on a known reference pressure. That is, in this case too, a positive absolute pressure is present Since the flow is driven based on the pressure differences through channel 22, a relative analysis as in FIG. 4 is also meaningful. As may be seen in FIG. 4, inlet opening 16 is located in a region 44, in which the static pressure is higher than in region 46, in which outlet opening 18 is located. In other words, the fluid medium has a higher static pressure in the vicinity of inlet opening 16 than in the vicinity of outlet opening 18. For instance, the static pressure is −0.75 Pa in the vicinity of outlet opening 18 and −0.65 Pa in the vicinity of inlet opening 16. The fluid medium is thereby pressed into inlet opening 16, and is then able to flow, counter to main flow direction 12 (e.g., in a direction anti-parallel to the main flow), through channel 22 on the inside of sensor housing 14, moisture sensor 24 being able to be acted upon, because of retaining element 28, by the moisture contained in the fluid medium. The fluid medium then flows out of channel 22 again through outlet opening 18 into the fluid medium flowing in main flow direction 12. In this context, inlet opening 16 is situated in such a way that the fluid medium is largely free of particles or droplets, since these, based on their inertia, cross the region of inlet opening 16 or do not even reach it in the first place, and keep flying in main flow direction 12, and do not get into channel 22. Consequently, the fluid medium which is guided past retaining element 28 of moisture sensor 24 is freed of particles and droplets, to the greatest extent. This avoids contamination of retaining element 24 and moisture sensor 24 is able to determine the moisture content exactly.

Returning to the illustration of FIG. 2, the form of flow shown in FIGS. 3 and 4 is shaped or formed by cover 20, in connection with the effect of sensor housing 14 jointly defining the field of flow, and it has approximately the shape of an airfoil profile between inlet opening 16 and outlet opening 18. In this context, it becomes clear from FIG. 2 that the fluid medium flowing in main flow direction 12 passes first outlet opening 18 and then reaches inlet opening 16. It is indicated, in particular, by arrow 30 how a partial flow of the fluid medium penetrates through inlet opening 16 into channel 22, in parallel to measuring surface 32 of moisture sensor 24, and flows counter (e.g., in a direction anti-parallel to the main flow) to main flow direction 12, sweeps over retaining element 28 and gets into the main flow of the fluid medium again. While the partial flow in channel 22 sweeps over retaining element 28, moisture is able to penetrate to measuring surface 32, so that moisture sensor 24 is able to determine the moisture content of the partial flow. Since the moisture content of the partial flow is approximately identical, or is identical after a certain response time, to the moisture content of the main flow, moisture sensor 24 is thus able to conclude upon the moisture content of the fluid medium flowing in the main flow direction 12 and determine it.

Additional possible specific embodiments of sensor system 10 according to the present invention are shown in FIGS. 5A through 5D. From here on, only the differences from the first specific embodiment are described, and identical components are provided with the same reference numerals.

Figure 5A:
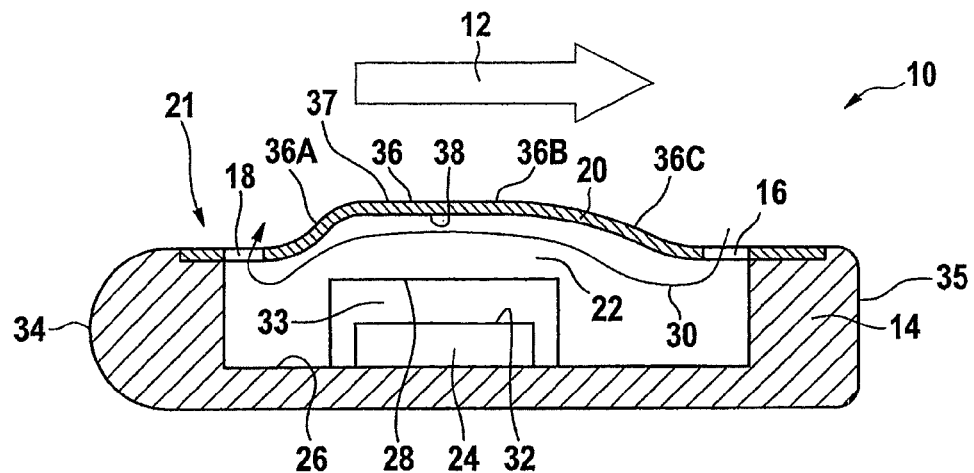
FIGS. 5A-5D show representations of additional possible specific embodiments of the sensor system.

In FIG. 5A, a leading edge 34 of sensor housing 14 is included in the design of the form of the flow shown in FIGS. 3 and 4. In particular, leading edge 34 is developed to be arched, the arching facing main flow direction 12, i.e. points counter to main flow direction 12.

Figure 5B:
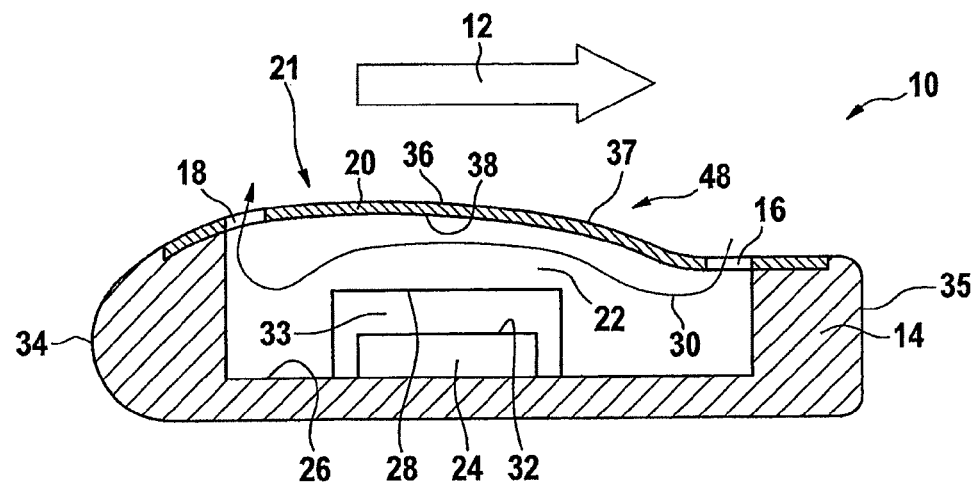

FIG. 5B shows a shape derived from a wing profile of sensor housing 14, i.e. the shape of the flow is influenced not by the shape of cover 20 between inlet opening 16 and outlet opening 18, but by the shape of the entire sensor housing 14 and cover 20. In particular, leading edge 34 is developed to be arched, the arching facing main flow direction 12, i.e. points counter to main flow direction 12. Furthermore, the entire cover 20 is arched, so that sensor housing 14 is developed in the shape of an airfoil profile 48.

Figure 5C:
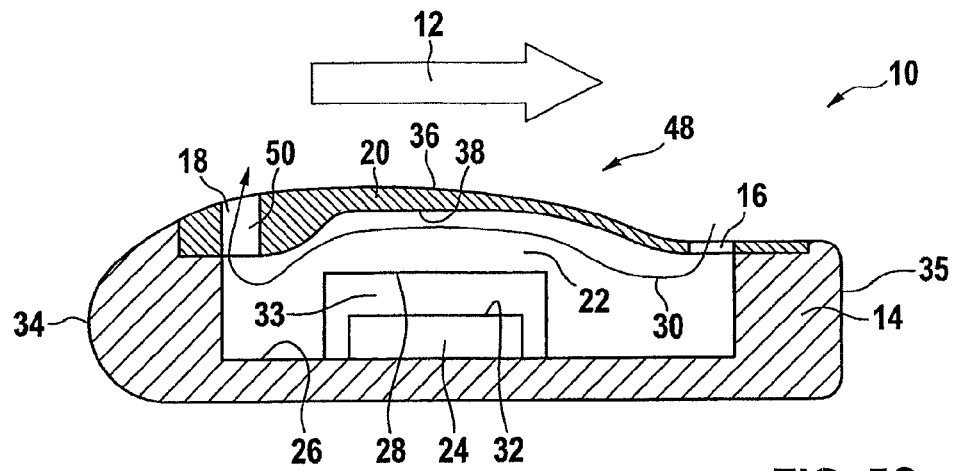

FIG. 5C shows an additional specific embodiment, in which the form of the flow is controlled by a chimney-like extension 50 in the area of outlet opening 18, particularly in the inner region, i.e. in channel 22. By a corresponding contouring of extension 50, the flowing over retaining element 28 is able to be controlled.

Figure 5D:
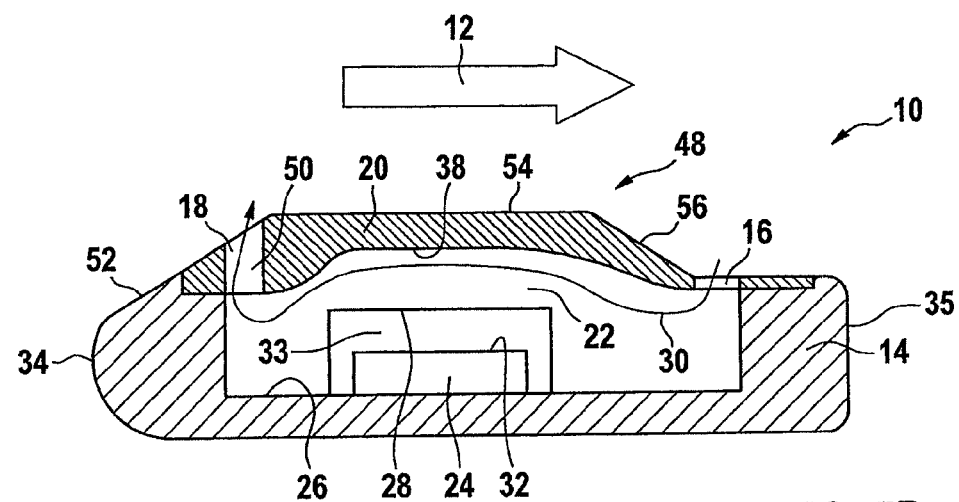

Finally, FIG. 5D shows an edgier specific embodiment of sensor housing 14 in comparison to sensor housing 14 of FIG. 5C, which may be easier to implement from a design point of view. In particular, cover 20 is developed so that, downstream from leading edge 34, it has a ramp-shaped section 52 which protrudes up to outlet opening 18, then, downstream from outlet opening 18 it has a section 54 running in parallel to main flow direction 12, and further downstream it has a section 56 which drops off, i.e. declines in the direction towards inlet opening 16.

Figure 6:
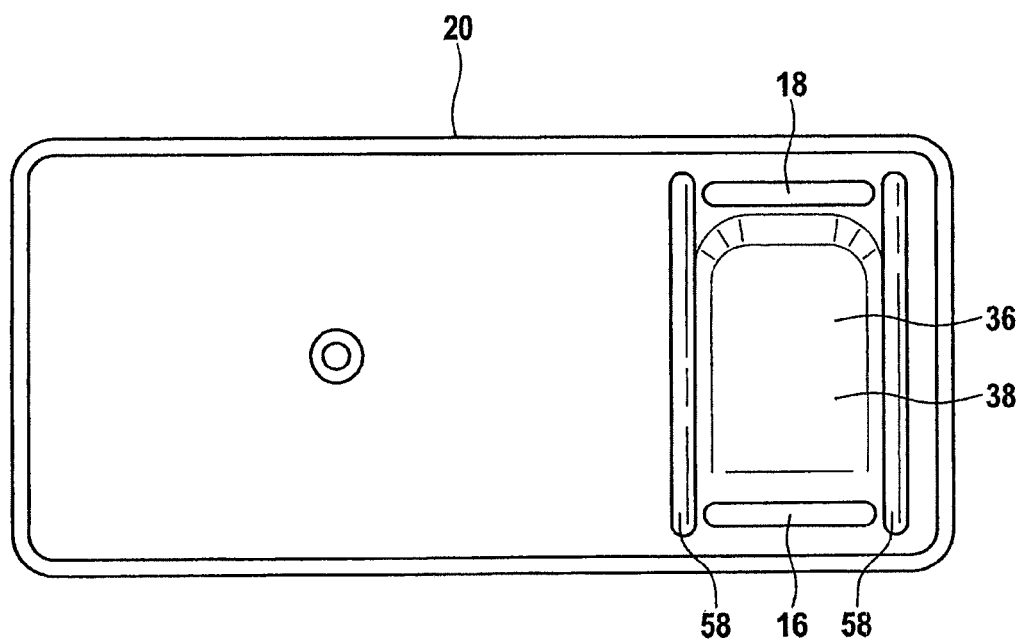
FIG. 6 shows a view from below a cover.

FIG. 6 shows a view from below as an example for cover 20. One may well recognize the shape of region 36 between inlet opening 16 and outlet opening 18. Based on the representation of cover 20, in a view from below, one may see area 36, in this case, as a depression, and one is looking at underside 38. A profiling of underside 38 deviating from upper side 36 is also conceivable based on a different thickness or material strength of the wall in this region. Furthermore, from the representation of FIG. 6, side walls 58 of channel 22 may be recognized, which border on channel 22. Side walls 58 run parallel to each other, as shown in FIG. 6. Side walls 58 may extend perpendicular to inlet opening 16 and outlet opening 18. Thereby, side walls 58 extend parallel to the fluid medium flowing in the direction of arrow 30. Side walls 58 may project rib-shaped, for example, from the underside of cover 20. Side walls 58 of channel 22 that are to be seen in the illustration of FIG. 6 ensure a flow guidance over retaining element 28 and prevent the flowing through of the electronic module region and possible recirculation regions in it.

Alternatively to the in-parallel development of side walls 58 shown in FIG. 6, convergent side walls 58 in channel 22 are also possible, which accelerate the flow from inlet opening 16 to retaining element 28 and then decelerate it again up to outlet opening 18, in order, after the flowing over retaining element 28, to avoid unnecessarily high wall friction losses in channel 22.

All the specific embodiments described above are able to be implemented in connection with additional sensors. For example, the moisture sensor is developed in a sensor housing of a hot film air mass sensor of the type described above.

What is claimed is:

1. A sensor system for determining a moisture content of a fluid medium flowing in a main flow direction, the fluid medium being an intake air of an internal combustion engine, the sensor system comprising:
   a sensor housing that has a rising leading edge located on an upper surface of the sensor housing and facing counter to the main flow direction of the flowing fluid medium, wherein the rising leading edge rises and moves away from a remaining portion of the housing;
   at least one moisture sensor situated in the sensor housing for determining the moisture content of the fluid medium; and
   at least one retaining element which is at least partially permeable to moisture;
   wherein an inlet opening is provided for channeling moisture into the interior of the sensor housing and to the moisture sensor, and wherein the retaining element is situated in the sensor housing in such a way that the moisture sensor is acted upon by the moisture channeled via the inlet opening and the retaining element, and wherein at least one outlet opening is provided which is situated separately from the inlet opening, the at least one outlet opening channeling moisture from the sensor housing into the flowing fluid medium, wherein:
   the inlet opening is located on a planar portion of the sensor housing that is parallel to the main flow direction,
   the rising leading edge is disposed between the inlet opening and the outlet opening along the main flow direction, and
   a maximum height of the rising edge is located closer to the outlet opening than the inlet opening, and
   the outlet opening is located one of:
      upstream of the rising leading edge, as viewed in the main flow direction, and
      on the rising leading edge.

2. The sensor system as recited in claim 1, wherein the inlet opening is located downstream from the outlet opening, as viewed in the main flow direction.

3. The sensor system as recited in claim 2, wherein the moisture sensor has a measuring surface, and wherein the sensor housing is configured in such a way that the fluid medium flows over the measuring surface of the moisture sensor in a direction that is anti-parallel to the main flow direction of the flowing fluid medium, within the sensor housing and between the inlet opening and the outlet opening.

4. The sensor system as recited in claim 3, wherein the sensor housing has a channel situated between the inlet opening and the outlet opening, and wherein the moisture sensor is situated in the channel.

5. The sensor system as recited in claim 4, wherein the sensor housing is configured so that the fluid medium flows faster in the vicinity of the outlet opening than in the vicinity of the inlet opening.

6. The sensor system as recited in claim 4, wherein the sensor housing is configured so that the fluid medium has a higher static pressure in the vicinity of the inlet opening than in the vicinity of the outlet opening.

7. The sensor system as recited in claim 4, wherein the sensor housing is configured to have essentially the shape of an airfoil profile, and wherein the inlet opening and the outlet opening are situated on an upper side of the airfoil profile.

8. The sensor system as recited in claim 7, wherein at least one of the inlet opening and the outlet opening is slot-shaped.

9. The sensor system as recited in claim 3, wherein:
a bypass channel which points counter to the main flow direction of the fluid medium is provided in the sensor housing;
the sensor housing has an inlet into the bypass channel and at least one outlet from the bypass channel of the sensor housing;
the sensor system further includes an additional sensor for determining at least one additional parameter of the fluid medium flowing through the bypass channel, the at least one additional parameter being an intake air mass of the internal combustion engine; and
the additional sensor has at least one sensor chip situated in the bypass channel for determining the additional parameter of the fluid medium.

10. The sensor system as recited in claim 3, wherein the outlet opening is located on the rising edge.

11. The sensor system as recited in claim 3, wherein the outlet opening and the inlet opening are located on the upper surface of the sensor housing.

12. The sensor system as recited in claim 3, wherein the inlet opening is located on the upper surface of the sensor housing and downstream of the rising leading edge, as viewed in the main flow direction.

13. The sensor system as recited in claim 3, wherein an axis of the inlet opening that is normal to the inlet opening is perpendicular to the main flow direction.

14. The sensor system as recited in claim 3, wherein the inlet opening and the outlet opening are located in a common plane that is parallel to the main flow direction and transverse to a cross-section of the sensor housing.

* * * * *